United States Patent [19]

Pastor et al.

[11] Patent Number: 5,137,951
[45] Date of Patent: Aug. 11, 1992

[54] SILYLATED HYDROXYAMINOMETHYLPHOSPHONATES AND STABILIZED COMPOSITIONS

[75] Inventors: Stephen D. Pastor, Danbury, Conn.; Ramanathan Ravichandran, Nanuet, N.Y.; Roger Meuwly, Givisiez, Switzerland.

[73] Assignee: Ciba-Geigy Corporation, Ardsley, N.Y.

[21] Appl. No.: 758,934

[22] Filed: Sep. 11, 1991

Related U.S. Application Data

[62] Division of Ser. No. 505,956, Apr. 6, 1990, Pat. No. 5,077,329.

[51] Int. Cl.$^5$ .............................. C08K 5/54; C07F 9/40
[52] U.S. Cl. .................................... 324/124; 252/499; 524/130; 524/131; 524/132; 556/404; 556/405; 554/4
[58] Field of Search ............... 524/124, 131, 132, 130; 556/404, 405; 252/49.9; 260/398.5

[56] References Cited

U.S. PATENT DOCUMENTS 3,483,178  12/1969  Crutchfield et al. ............ 558/158
3,933,346  1/1976   Gaertner ........................ 558/175
4,753,972  6/1988   Ravichandran ................. 558/175

FOREIGN PATENT DOCUMENTS 1-100182  4/1989  Japan .

OTHER PUBLICATIONS

M. P. Osipova et al., Deposited Doc. SPSTL 232 Khp-D80 (USSR), Chem. Abst. 97, 110110w (1982).
K. A. Petrov et al., Zh. Obshch. Khim. 49, 590 (1979).
M. S. Skorobogatova et al., I zv. Alkad. Nauk. SSSR, Ser. Khim (1979) 1867.
A. Muktanov et al., Izv. Akad. Nauk SSSR, Ser. Khim (1976) 2816.
A. Alberti et al., Tetrahedron, 40, 4955 (1984).
J. M. J. Tronchet et al., Carbohydrate Research 136,375 (1985).
R. Huber et al., (A. Vasella et al.), Helv. Chim. Acta, 68, 1730 (1985).
Y. Yamada et al., Tetrahedron Letters, 29, 663 (1988).

*Primary Examiner*—Veronica P. Hoke
*Attorney, Agent, or Firm*—Luther A. R. Hall

[57] ABSTRACT

Hydroxyaminomethylphosphonates of formula I

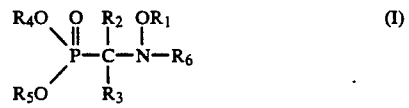

where $R_1$ to $R_5$ are independently hydrogen, alkyl, cycloalkyl, aryl or phenylalkyl, $R_6$ has the same meanings except for hydrogen, and $R_1$ can also be trialkylsilyl, are useful stabilizers for organic materials subject to oxidative, thermal or actinic induced degradation.

11 Claims, No Drawings

SILYLATED HYDROXYAMINOMETHYLPHOSPHONATES AND STABILIZED COMPOSITIONS

This is a divisional of Ser. No. 505,956, filed Apr. 6, 1990, now U.S. Pat. No. 5,077,329.

The instant invention pertains to selected hydroxyaminomethylphosphonates and to their use as stabilizers for a variety of organic materials.

BACKGROUND OF THE INVENTION

Low molecular weight hydroxyaminomethylphosphonates have been described in the literature as seen by the following publications:
1. M. P. Osipova et al., Deposite Doc. SPSTL 232 khp-D80 (USSR); Chem. Abst. 97, 110110 (1982);
2. K. A. Petrov et al., Zh. Obshch. Khim, 49, 590 (1979);
3. M. S. Skorobogatova et al., Izv. Akad. Nauk. SSSR, Ser. Khim. 1979, 1867;
4. A. Muktarov et al., Izv. Akad. Nauk. SSSR, Ser. Khim. 1976, 2816;
5. A. Alberti et al., Tetrahedron, 40, 4955 (1984);
6. J. M. J. Tronchet et al., Carbohydrate Research, 136, 375 (1985);
7. A. Vasella et al., Helv. Chim. Acta, 68, 1730 (1985); and
8. Y. Yamada et al., Tetrahedron Letters, 29, 663 (1988).

U.S. Pat. No. 3,933,946 describes N-hydroxy-N-phosphonomethylglycine esters which are useful as herbicides and plant growth regulators.

The use of hydroxyaminomethylphosphonates as stabilizers for organic materials is not described or suggested in the prior art. Additionally the compounds of formula I where $R_4$, $R_5$ and $R_6$ are alkyl having at least 12 carbon atoms are novel. The instant compounds where $R_1$ is a substituted silyl moiety are also novel.

OBJECTS OF THE INVENTION

One object of the instant invention is to provide compositions stabilized against the deleterious effects of oxygen, heat and/or light containing an effective amount of the instant compounds.

Another object of the instant invention to provide new and novel compounds embraced within the scope of formula I.

DETAILED DISCLOSURE

The instant invention pertains to a composition stabilized against the deleterious effects of oxygen, heat or light which comprises (a) an organic material subject to oxidative, thermal or actinic induced degradation, and (b) an effective stabilizing amount of a compound of formula I

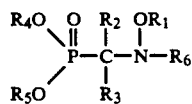

wherein $R_1$ is hydrogen, alkyl of 1 to 36 carbon atoms, cycloalkyl of 5 to 12 carbon atoms, aryl of 6 to 10 carbon atoms, said aryl substituted by one or two alkyl of 1 to 8 carbon atoms, phenylalkyl of 7 to 15 carbon atoms, or (R)(R')(R'')Si- or (R)(R')(R'')Si-OCH$_2$- where R, R' and R'' are independently alkyl of 1 to 8 carbon atoms, aryl of 6 to 10 carbon atoms or phenylalkyl of 7 to 15 carbon atoms, $R_2$ and $R_3$ are independently hydrogen, alkyl of 1 to 36 carbon atoms, aryl of 6 to 10 carbon atoms, or phenylalkyl of 7 to 15 carbon atoms, $R_4$ and $R_5$ are independently hydrogen, alkyl of 1 to 36 carbon atoms, cycloalkyl of 5 to 12 carbon atoms, aryl of 6 to 10 carbon atoms, said aryl substituted by one or two alkyl of 1 to 8 carbon atoms or phenylalkyl of 7 to 15 carbon atoms, or an alkali metal or alkaline earth metal salt, and $R_6$ is alkyl of 1 to 36 carbon atoms, cycloalkyl of 5 to 12 carbon atoms, aryl of 6 to 10 carbon atoms, said aryl substituted by one or two alkyl of 1 to 8 carbon atoms, phenylalkyl of 7 to 15 carbon atoms, or is a group of formula II

wherein $R_2$, $R_3$, $R_4$ and $R_5$ have the meanings given above.

The preferred embodiments of the compounds of formula I are those where $R_1$ is hydrogen, alkyl of 4 to 18 carbon atoms, cycloalkyl of 5 to 7 carbon atoms, phenyl or phenyl substituted by alkyl of 1 to 4 carbon atoms, or benzyl, or $R_1$ is (R)(R')(R'')Si- or (R)(R')(R'')Si-OCH$_2$- where R, R' and R'' are independently alkyl of 1 to 4 carbon atoms or phenyl, $R_2$ and $R_3$ are independently hydrogen, alkyl of 1 to 17 carbon atoms or phenyl, $R_4$ and $R^5$ are independently hydrogen, alkyl of 1 to 18 carbon atoms, cycloalkyl of 5 to 7 carbon atoms, phenyl or phenyl substituted by alkyl of 1 to 4 carbon atoms, or benzyl, and $R_6$ is alkyl of 4 to 18 carbon atoms, benzyl or is a group of formula II where $R_2$, $R_3$, $R_4$ and $R_5$ have the preferred meanings given above.

The most preferred embodiments of the compounds of formula I are those where $R_1$ is hydrogen or alkyl of 4 to 12 carbon atoms, or $R_1$ is (R)(R')(R'')Si- or (R)(R')(R'')Si-OCH$_2$- where R, R' and R'' are independently methyl, tert-butyl or phenyl, $R_2$ is hydrogen or methyl, $R_3$ is hydrogen, alkyl of 1 to 17 carbon atoms or phenyl, $R_4$ and $R_5$ are independently hydrogen, alkyl of 1 to 18 carbon atoms, phenyl or benzyl, and $R_6$ is alkyl of 4 to 18 carbon atoms, benzyl or a group of formula II where $R_2$, $R_3$, $R_4$ and $R_5$ have the most preferred meanings given above.

Most preferably $R_4$ and $R_5$ are the same.

Still more preferred are the compounds of formula I where $R_1$ is hydrogen or alkyl of 4 to 12 carbon atoms; $R_2$ is hydrogen; $R_3$ is alkyl of 11 to 17 carbon atoms; $R_4$ and $R_5$ are each alkyl of 4 to 18 carbon atoms or benzyl; and $R_6$ is alkyl of 10 to 18 carbon atoms.

When $R_1$, $R_2$, $R_3$, $R_4$, $R_5$, $R_6$, R, R' or R'' is alkyl, the alkyl depending on the carbon atom range cited for each group includes, for example, methyl, ethyl, isopropyl, n-butyl, sec-butyl, tert-butyl, isoamyl, tert-amyl, n-hexyl, 2-ethylhexyl, isooctyl, n-octyl, nonyl, decyl, undecyl, lauryl, tridecyl, tetradecyl, hexadecyl, heptadecyl, octadecyl, eicosyl and branched isomers thereof.

Cycloalkyl of 5 to 12 carbon atoms includes, for example, cyclopentyl, cyclohexyl, cycloheptyl, cyclooctyl, and cyclododecyl.

When aryl of 6 to 10 carbon atoms is disclosed, such groups include, for example, phenyl or naphthyl. Said aryl substituted by one or two alkyl groups includes, for example, tolyl, xylyl, mesityl or ethylphenyl.

Phenylalkyl of 7 to 15 carbon atoms includes, for example, benzyl, phenethyl, α-methylbenzyl or β-methylphenethyl.

When $R_4$ and $R_5$ are an alkali metal or alkaline earth metal salt, they are $Na^+$, $K^+$, $Li^+$, $Ca^{++}$, $Mg^{++}$ or $Sr^{++}$.

The compositions where component (a) is a synthetic polymer are especially part of this invention, most particularly when the synthetic polymer is a polyolefin such as polypropylene.

The instant compounds are effective stabilizers for organic materials or compositions of matter comprising organic materials in that they reduce degradation resulting from long term oxidative and/or thermal aging and effectively protect said materials from actinic radiation.

In addition, the instant compounds show little tendency to evaporate or sublime from the organic compositions during thermal processing. Thus, the instant compounds are effective process stabilizers for organic polymers processed at elevated temperatures.

The instant compounds of formula I are conveniently prepared by the reaction of a monosubstituted hydroxylamine, an aldehyde or ketone and a dialkyl or dibenzyl phosphite; or by the reaction of an appropriate α-nitrone, a trialkyl or tribenzyl phosphite and an alkyl or benzyl halide.

The starting materials for making the instant compounds are largely items of commerce or can be made by known methods. The α-nitrones themselves are readily prepared by the controlled oxidation of a secondary amine (such as hydrogenated tallow amine) or by reaction of an aldehyde and a substituted hydroxylamine.

Another aspect of the instant invention are the compounds of formula I

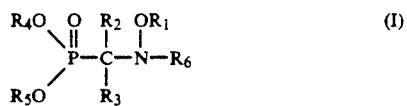

wherein $R_1$ is (R)(R')(R'')Si- or (R)(R')(R'')Si-OCH$_2$- where R, R' and R'' are independently alkyl of 1 to 18 carbon atoms, aryl of 6 to 10 carbon atoms or phenylalkyl of 7 to 15 carbon atoms, and $R_2$, $R_3$, $R_4$, $R_5$ and $R_6$ are as defined above.

The preferred embodiments of these silyl compounds are those where R, R' and R'' are independently alkyl of 1 to 4 carbon atoms or phenyl, and $R_2$ to $R_6$ have the preferred definitions given supra.

The most preferred embodiments of these silyl compounds are those where R, R' and R'' are independently methyl, tert-butyl or phenyl, and $R_2$ to $R_6$ have the most preferred definitions given supra.

Still another aspect of the instant invention are the compounds of formula I

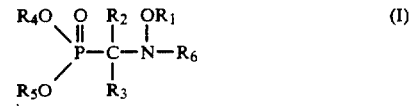

wherein $R_1$ is hydrogen, alkyl of 1 to 36 carbon atoms, cycloalkyl of 5 to 12, carbon atoms, aryl of 6 to 10 carbon atoms, said aryl substituted by one or two alkyl of 1 to 8 carbon atoms or phenylalkyl of 7 to 15 carbon atoms, $R_2$ and $R_3$ are independently hydrogen, alkyl of 1 to 36 carbon atoms, aryl of 6 to 10 carbon atoms or phenylalkyl of 7 to 15 carbon atoms, $R_4$ and $R_5$ are independently alkyl of 12 to 36 carbon atoms, and $R_6$ is alkyl of 12 to 36 carbon atoms, benzyl or a group of formula II where $R_2$, $R_3$, $R_4$ and $R_5$ are as defined above.

The preferred embodiments of these long alkyl substituted compounds are those where $R_1$ is hydrogen, alkyl of 4 to 18 carbon atoms, cycloalkyl of 5 to 7 carbon atoms, phenyl, phenyl substituted by alkyl of 1 to 4 carbon atoms, or is benzyl, $R_2$ and $R_3$ are independently hydrogen, alkyl of 1 to 17 carbon atoms or phenyl, $R_4$ and $R_5$ are independently alkyl of 12 to 18 carbon atoms, and $R_6$ is alkyl of 12 to 18 carbon atoms, benzyl or a group of formula II where $R_2$, $R_3$, $R_4$ and $R_5$ are as defined above.

Still more preferred embodiments of these long alkyl substituted compounds are those where $R_1$ is hydrogen or alkyl of 4 to 12 carbon atoms, $R_2$ is hydrogen or methyl, $R_3$ is hydrogen, alkyl of 1 to 17 carbon atoms or phenyl, $R_4$ and $R_5$ are each alkyl of 12 to 18 carbon atoms, and $R_6$ is alkyl of 12 to 18 carbon atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α, β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants
    1.1. Alkylated monophenols, for example,
2,6-di-tert-butyl-4-methylphenol
2-tert.butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol
    1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
    1.3. Hydroxylated thiodiphenyl ethers, for example
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
    1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.
    1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid di-octadecyl ester
3,5-di-tert-butyl-4-hydroxybenzyl-phosphoric acid monoethyl ester, calcium-salt
    1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate
    1.7. Esters of β-(3,5-di-tert-butyl-4-hydroxyphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide
    1.8. Esters of β-(5-tert-butyl-4-hydroxy-3-methylphenyl)propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid
diamide
    1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 2. UV absorbers and light stabilizers
    2.1. 2-(2'-Hydroxyphenyl)-benzotriazoles, for example the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxyocta-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone).

2.7. Oxalic acid diamides, for example, 4,4'-dioctyloxyoxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl]-6-phenyl-s-triazine; 2,4-bis[2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The following examples are presented for the purpose of illustration only and are not to be construed to limit the nature or scope of the instant invention in any manner whatsoever.

EXAMPLE 1

Dibenzyl P-(N-Benzyl-N-hydroxyaminomethyl)phosphonate

A mixture of 2.0 g (12.5 mmol) of N-benzylhydroxylamine hydrochloride, 0.75 g (25 mmol) of paraformaldehyde, 1.0 g (12 mmol) of sodium bicarbonate and 40 ml of tetrahydrofuran (THF) is stirred at 59° C. for one hour. To the resultant mixture is then added dropwise over a three-hour period a solution of 3.6 g (13.7 mmol) of dibenzyl phosphite in 40 ml of THF. The reaction mixture is then stirred for 14 hours at 55° C. The reaction mixture is concentrated in vacuo to 20 ml volume and 500 ml of ethyl acetate is added. The organic phase is separated and washed sequentially with a saturated solution of sodium bicarbonate and a saturated solution of sodium chloride. The organic phase is dried over anhydrous magnesium sulfate and the solvent removed in vacuo. The residue is purified by column chromatography (silica gel, 20:1, methylene chloride:ethyl acetate eluent) followed by recrystallization from a mixture of methylene chloride, ethyl acetate and hexane to give 1.95 g (40% yield) of a white solid melting at 62°–64° C.

Analysis: Calcd for $C_{22}H_{24}NO_4P$: C, 66.5; H, 6.1; N, 3.5; P, 7.8. Found: C, 66.5; H, 6.2; N, 3.5; P, 8.1.

EXAMPLE 2

Dibenzyl P-(N-tert-Butyl-N-hydroxyaminomethyl)phosphonate

Using the procedure of Example 1, the above-named compound is prepared from 5.0 g (40 mmol) of N-tert-butylhydroxylamine hydrochloride, 2.4 g (80 mmol) of paraformaldehyde, 9.0 g (41 mmol) of dibenzyl phosphite, 3.0 g (40 mmol) of sodium bicarbonate and 200 ml of tetrahydrofuran (THF) by heating at 55° C. for 14 hours. The residue is purified by recrystallization from a mixture of methylene chloride and hexane to give 9.2 g (64% yield) of a white solid melting at 106°–107° C.

Analysis: Calcd for $C_{19}H_{26}NO_4P$: C, 62.8; H, 7.2; N, 3.8; P, 8.5. Found: C, 62.6; H, 7.1; N, 3.8; P, 8.9.

EXAMPLE 3

Dibenzyl P-[2-(N-Benzyl-N-hydroxyamino)isopropyl]phosphonate

Using the procedure of Example 1, the above-named compound is prepared from 5.0 g (31 mmol) of N-benzylhydroxylamine hydrochloride, 4.4 ml (60 mmol) of acetone, 8.8 g (40 mmol) of dibenzyl phosphite, 2.5 g (30 mmol) of sodium bicarbonate and 200 ml of THF by heating at 55° C. for 24 hours. The residue is purified by recrystallization from a mixture of methylene chloride and hexane to give 5.6 g (43% yield) of a white solid melting at 116°–117° C.

Analysis: Calcd for $C_{24}H_{28}NO_4P$: C, 67.8; H, 6.6; N, 3.3; P, 7.3. Found: C, 67.6; H, 6.6; N, 3.2; P, 7.2.

EXAMPLE 4

Dimethyl P-(N-Benzyl-N-hydroxyaminomethyl)phosphonate

Using the procedure of Example 1, the above-named compound is prepared from 5.0 g (31 mmol) of N-benzylhydroxylamine hydrochloride, 1.8 g (60 mmol) of paraformaldehyde, 3.7 ml (40 mmol) of dimethyl phosphite, 2.5 g (30 mmol) of sodium bicarbonate and 350 ml of THF by heating at 55° C. for seven hours. The residue is purified by column chromatography (silica gel, methylene chloride:ethyl acetate eluent) to give 6.1 g (80% yield) of a viscous colorless liquid.

Analysis: Calcd for $C_{10}H_{16}NO_4P$: C, 49.0; H, 6.6; N, 5.7; P, 12.6. Found: C, 48.6; H, 6.5; N, 5.7; P, 12.6.

EXAMPLE 5

N,N-Bis(dibenzyloxyphosphinylmethyl)hydroxylamine

Using the procedure of Example 1, the above-named compound is prepared from 1.98 g (29 mmol) of hydroxylamine hydrochloride, 3.4 g (114 mmol) of paraformaldehyde, 15.0 g (58 mmol) of dibenzyl phosphite, 1.17 g (14 mmol) of sodium bicarbonate and 200 ml of THF by heating at 55° C. for 14 hours. The residue is purified by column chromatography (silica gel, 2:1:0.1 ethyl acetate:toluene:ethyl alcohol eluent) to give 8.1 g (49% yield) of a white solid melting at 71°–73° C.

Analysis: Calcd for $C_{30}H_{33}NO_7P_2$: C, 62.0; H, 5.7; N, 2.4. Found: C, 62.3; H, 5.5; N, 2.4.

EXAMPLE 6

Dibenzyl P-[α-(N-Benzyl-N-hydroxyamino)benzyl]phosphonate

Using the procedure of Example 1, the title compound is prepared from 15.0 g (94 mmol) of N-benzylhydroxylamine hydrochloride, 10.6 g (100 mmol) of benzaldehyde, 26.7 g (100 mmol) of dibenzyl phosphite, 3.78 g (45 mmol) of sodium bicarbonate and 300 ml of THF by heating at 60° C. for four hours. The residue is purified by column chromatography (silica gel, 2.5:1 hexane:ethyl acetate eluent) followed by recrystallization from a mixture of methylene chloride and hexane to give 5.6 g (13% yield) of a white solid melting at 116°–118° C.

Analysis: Calcd for $C_{28}H_{28}NO_4P$: C, 71.0; H, 6.0; N, 3.0. Found: C, 71.2; H, 6.0; N, 2.9.

EXAMPLE 7

Didodecyl P-[α-(N-Benzyl-N-dodecyloxyamino)benzyl]phosphonate

A mixture of 5.0 g (23 mmol) of N-benzylidenebenzylamine N-oxide, 17.6 g (30 mmol) of tri-n-dodecyl phosphite and 29.6 g (100 mmol) of n-dodecyl iodide is heated at 70° C. for 24 hours. The reaction mixture is concentrated in vacuo and the residue is purified by HPLC (4:1 hexane:ethyl acetate eluent) followed by flash chromatography (methylene chloride eluent) to give 5.1 g (28% yield) of the title compound as a white solid melting at 38°–40° C.

Analysis: Calcd for $C_{50}H_{88}NO_4P$: C, 75.2; H, 11.1; N, 1.8; P, 3.9. Found: C, 75.3; H, 11.1; N, 1.6; P, 4.0.

EXAMPLE 8

Dibutyl P-[1-(N-Octadecyl-N-butoxyamino)octadecyl]phosphonate

Following the procedure of Example 7, the title compound is prepared from 10.0 g (18 mmol) of N-(1-octadecylidene)octadecylamine N-oxide, 7.0 g (28 mmol) of tri-n-butyl phosphite and 5.15 g (28 mmol) of n-butyl iodide by heating at 70° C. for 16 hours. The residue is purified by flash chromatography (10:1 hexane:ethyl acetate eluent) followed by HPLC to give 4.9 g (35% yield) of the title compound as a white solid melting at 38°–40° C.

Analysis: Calcd for $C_{48}H_{100}NO_4P$: C, 73.3; H, 12.8; N, 1.8. Found: C, 73.4; H, 12.3; N, 1.6.

EXAMPLE 9

Didodecyl P-[1-(N-Octadecyl-N-dodecyloxyamino)octadecyl]-phosphonate

Following the procedure of Example 7, the title compound is prepared from 2.5 g (4.6 mmol) of N-(1-octadecylidene)-octadecylamine N-oxide, 2.9 g (5.0 mmol) of tri-n-dodecylphosphite, 3.0 g (10 mmol) of n-dodecyl iodide, 20 ml of acetonitrile and 40 ml of toluene by heating at 70° C. for 24 hours. The residue is purified by flash chromatography (10:1 hexane:ethyl acetate eluent) to give 1.5 g (29% yield) of the title compound as a white, low melting wax.

Analysis: Calcd for $C_{72}H_{148}NO_4P$: C, 77.0; H, 13.3; N, 1.3. Found: C, 77.2; H, 13.3; N, 1.1.

EXAMPLE 10

Dibenzyl P-(N-Benzyl-N-tert-butyldimethylsilyloxyaminomethyl)phosphonate and Dibenzyl P-(N-Benzyl-N-tert-butyldimethylsilyloxymethoxyaminomethyl)phosphonate To a mixture of 10.0 g (62 mmol) of N-benzylhydroxylamine hydrochloride, 3.15 g (125 mmol) of paraformaldehyde, 3.4 g (40 mmol) of sodium bicarbonate and 200 ml of tetrahydrofuran (THF) at 60° C. is added dropwise over a two-hour period a solution of 16.5 g (63 mmol) of dibenzyl phosphite in 50 ml of THF. The reaction mixture is stirred for four hours at 60° C. and then concentrated under reduced pressure to a volume of 50 ml before 500 ml of ethyl acetate is added. The organic phase is separated and washed sequentially with a saturated solution of sodium carbonate and a saturated solution of sodium chloride. The organic phase is then dried over anhydrous magnesium sulfate. The solvent is then removed in vacuo. The residue is dissolved in 150 ml of N,N-dimethylformamide and to the resulting solution is added 16.8 g (248 mmol) of imidazole. To this solution at room temperature is added dropwise 18.9 g (125 mmol) of tert-butyldimethylsilyl chloride. The reaction mixture is stirred for ten hours at room temperature. To the reaction mixture is then added 1000 ml of ethyl acetate and the solution washed successively with a saturated solution of sodium bicarbonate and a saturated solution of sodium chloride. The organic phase is dried over anhydrous magnesium sulfate and the solvent then removed in vacuo. The residue is purified by column chromatography (silica gel, 3:1 hexane:ethyl acetate eluent) followed by HPLC (3:1 hexane:ethyl acetate eluent) to give the two title compounds.

The first-named title compound is obtained in a yield of 7.5 g (24%) as a white solid melting at 65°-66° C.

Analysis: Calcd for $C_{28}H_{38}NO_4PSi$: C, 65.7; H, 7.5; N, 2.7; P, 6.0. Found: C, 65.7; H, 7.5; N, 2.6; P, 6.1.

The second-named title compound is obtained in a yield of 8.1 g (24%) as a colorless liquid.

Analysis: Calcd for $C_{29}H_{40}NO_5PSi$: C, 64.3; H, 7.4; N, 2.6; P, 5.7. Found: C, 64.2; H, 7.3; N, 2.5; P, 5.5.

EXAMPLE 11

Phenyl P-(N-Benzyl-N-hydroxyaminomethyl)phosphonate

To a solution of 4.6 g (38 mmol) of N-benzylhydroxylamine in 25 ml of acetonitrile is added a solution of 3.05 ml (38 mmol) of a 37% aqueous solution of formaldehyde in 2 ml of acetonitrile. The reaction mixture is stirred at room temperature for five minutes and then to the resultant mixture is added dropwise over a 5-minute period a solution of 8.8 g (38 mmol) of diphenyl phosphite in 2 ml of acetonitrile. The reaction mixture is stirred overnight and the resultant precipitate is collected by filtration. The crude product is purified by trituration in 150 ml of boiling acetonitrile to give 6.9 g (64% yield) of the title compound as a white solid melting at 156°-157° C.

Analysis: Calcd for $C_{14}H_{16}NO_4P$: C, 57.3; H, 5.5; N, 4.8; P, 10.6. Found: C, 57.1; H, 5.4; N, 4.9; P, 10.5.

EXAMPLE 12

Processing Stabilization of Polypropylene at 260° C.

The test stabilizers are solvent blended into unstabilized polypropylene (PROFAX 6501 Himont) which already contains 0.1% by weight of calcium stearate. After removal of the solvent under reduced pressure, the stabilized polypropylene is subjected to repeated melt extrusions at 260° C. and the melt flow rate (MFR) is measured after the first and fifth extrusions. The MFR is determined by the ASTM method 1238 condition L. The molecular weight of polypropylene falls as thermal degradation occurs so a minimum change in MFR indicates superior thermal stabilization of the polymer by the test additive. The results are seen in Table I below.

TABLE I

| Additive of Example | Concentration (% by weight) | Melt Flow Rate after Extrusion | |
|---|---|---|---|
| | | 1st | 5th |
| None* | — | 10.7 | 30 |
| AO A** | 0.1 | 4.3 | 12.7 |
| Example 1 | 0.1 | 2.1 | 3.7 |
| Example 5 | 0.1 | 4.2 | 13.5 |
| AO A plus | 0.1 | 2.6 | 9.6 |
| Example 1 | 0.1 | | |

*Base resin contains 0.1% by weight of calcium stearate.
**AO A is neopentanetetrayl tetrakis(3,5-di-tert-butyl-4-hydroxyhydrocinnamate).

The instant stabilizers can provide polypropylene better thermal stabilization protection than does a phenolic antioxidant.

EXAMPLE 13

Oxidation Stability of Stabilized Polypropylene

The oxidation stability of milled polypropylene samples, containing the indicated test stabilizers, is measured on plaques of 25 mil (0.635 mm) thickness on exposure to air in a forced draft air oven at 150° C. The color developed during this exposure of the plaques is determined by the yellowness index (YI) values after various hours of exposure at 150° C. according to ASTM method D1925. These data are shown in Table II below. The lower is the YI value the less is the color developed and the better is the color stabilization provided by the test stabilizer.

TABLE II

| Additive of Example (0.05% by weight)* | Yellowness Index after Hours at 150° C. | | | | |
|---|---|---|---|---|---|
| | 0 | 38 | 85 | 151 | 264 |
| Control* | 7.1 | 11.9 | 20.1 | 31.6 | 44.3 |
| Example 1** | 5.0 | 7.8 | 11.4 | 16.5 | 25.7 |
| Example 2** | 6.6 | 9.4 | 13.6 | 19.9 | 28.0 |
| Example 3** | 6.8 | 9.9 | 13.6 | 19.9 | 28.0 |
| Example 4** | 9.5 | 15.4 | 20.5 | 25.5 | 34.8 |

TABLE II-continued

| Additive of Example (0.05% by weight)* | Yellowness Index after Hours at 150° C. | | | | |
|---|---|---|---|---|---|
| | 0 | 38 | 85 | 151 | 264 |
| Example 6** | 4.9 | 7.7 | 10.5 | 14.8 | 23.1 |

*Control contains 0.1% by weight calcium stearate and 0.1% by weight of neopentanetetrayl tetrakis(3,5-di-tert-butyl-4-hydroxyhydrocinnamate).
**Each example also contains the same components as the control.

The instant stabilizers provide polypropylene with better resistance to discoloration than does a phenolic antioxidant alone.

EXAMPLE 14

Color Stabilization of Polypropylene

This example illustrates the color stabilizing effectiveness of the instant compounds in combination with a phenolic antioxidant in polypropylene. Polypropylene stabilized according to the procedure of Example 12 is extruded at 260° C. and the resin pellets obtained after the first extrusion are compression molded at 193° C. into 125 mil (3.2 mm) thick plaques. Plaque yellowness index (YI) values are determined according to ASTM method D1925. The results are shown on Table III below.

TABLE III

| Additive of Example | Concentration (% by weight) | Yellowness Index After 1st Extrusion |
|---|---|---|
| None* | — | 2.2 |
| AO A** | 0.1 | 8.4 |
| Example 7 | 0.1 | 1.9 |
| Example 9 | 0.1 | 2.1 |
| AO A plus | 0.1 | |
| Example 1 | 0.05 | 2.9 |
| AO A plus | 0.1 | |
| Example 2 | 0.05 | 2.6 |
| AO A plus | 0.1 | |
| Example 5 | 0.05 | 4.4 |
| AO A plus | 0.1 | |
| Example 7 | 0.05 | 4.6 |
| AO A plus | 0.1 | |
| Example 9 | 0.05 | 5.7 |

*Control contains 0.1% by weight of calcium stearate.
**AO A is neopentanetetrayl tetrakis(3,5-di-tert-butyl-4-hydroxyhydrocinnamate).

The combination of an instant compound with a phenolic antioxidant greatly reduces the amount of color developed in the stabilized polypropylene compared to the use of a phenolic antioxidant alone.

What is claimed is:

1. A composition stabilized against the deleterious effects of oxygen, heat or light which comprises
   (a) an organic material subject to oxidative, thermal or actinic degradation, which is a naturally occurring or synthetic fat, wax, oil or polymer, and
   (b) an effective stabilizing amount of a compound of formula I

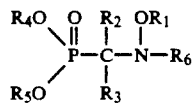

(I)

wherein
$R_1$ is $(R)(R')(R'')Si—$ or $(R)(R')R'')Si—OCH_2—$ where R, R' and R" are independently alkyl of 1 to 8 carbon atoms, aryl of 6 to 10 carbon atoms or phenylalkyl of 7 to 15 carbon atoms, $R_2$ and $R_3$ are independently hydrogen, alkyl of 1 to 36 carbon atoms, aryl of 6 to 10 carbon atoms or phenylalkyl of 7 to 15 carbon atoms, $R_4$ and $R_5$ are independently hydrogen, alkyl of 1 to 36 carbon atoms, cycloalkyl of 5 to 12 carbon atoms, aryl of 6 to 10 carbon atoms, said aryl substituted by one or two alkyl of 1 to 8 carbon atoms, phenylalkyl of 7 to 15 carbon or an alkali metal or alkaline earth metal salt, and $R_6$ is alkyl of 1 of 36 carbon atoms, cycloalkyl of 5 to 12 carbon atoms, aryl of 6 to 10 carbon atoms, said aryl substituted by one or two alkyl of 1 to 8 carbon atoms, or phenylalkyl of 7 to 15 carbon atoms, or $R_6$ is a group of formula II

(II)

wherein $R_2$, $R_3$, $R_4$ and $R_5$ are as defined above.

2. A composition according to claim 1 wherein the organic material is a synthetic polymer.

3. A composition according to claim 2 wherein the synthetic polymer is a polyolefin.

4. A composition according to claim 3 wherein the synthetic polymer is polypropylene.

5. A composition according to claim 1 where in the compound of formula I
   $R_1$ is $(R)(R')(R'')Si—$ or $(R)(R')(R'')Si—OCH_2—$ where R, R' and R" are independently alkyl of 1 to 4 carbon atoms or phenyl,
   $R_2$ and $R_3$ are independently hydrogen, alkyl of 1 to 17 carbon atoms or phenyl,
   $R_4$ and $R_5$ are independently hydrogen, alkyl of 1 to 18 carbon atoms, cycloalkyl of 5 to 7 carbon atoms, phenyl, phenyl substituted by alkyl of 1 to 4 carbon atoms, or benzyl, and
   $R_6$ is alkyl of 4 to 18 carbon atoms, benzyl or a group of formula II where $R_2$, $R_3$, $R_4$ and $R_5$ have the meanings above.

6. A composition according to claim 5 wherein $R_1$ is $(R)(R')(R'')Si—$ or $(R)(R')(R'')Si—OCH_2—$ where R, R' and R" are independently methyl, tert-butyl or phenyl, $R_2$ is hydrogen or methyl, $R_3$ is hydrogen, alkyl of 1 to 17 carbon atoms or phenyl, $R_4$ and $R_5$ are independently hydrogen, alkyl of 1 to 18 carbon atoms, phenyl or benzyl, and $R_6$ is alkyl of 4 to 18 carbon atoms, benzyl or a group of formula II where $R_2$, $R_3$, $R_4$ and $R_5$ are as defined above.

7. A compound of formula I

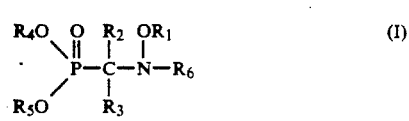

(I)

wherein
$R_1$ is $(R)(R')(R'')Si—$ or $(R)(R')(R'')Si—OCH_2—$ where R, R' and R" are independently alkyl of 1 to 8 carbon atoms, aryl of 6 to 10 carbon atoms or phenylalkyl of 7 to 15 carbon atoms, $R_2$ and $R_3$ are independently hydrogen, alkyl of 1 to 36 carbon atoms, aryl of 6 to 10 carbon atoms or phenylalkyl of 7 to 15 carbon atoms, $R_4$ and $R_5$ are independently hydrogen, alkyl of 1 to 36 carbon atoms, cycloalkyl of 5 to 12 carbon atoms, aryl of 6 to 10 carbon atoms, said aryl substituted by one or two alkyl of 1 to 8 carbon atoms, phenylalkyl of 7 to 15 carbon atoms, or an alkali metal or alkaline earth metal salt, and $R_6$ is alkyl of 1 to 36 carbon atoms, cycloalkyl of 5 to 12 carbon atoms, aryl of 6 to 10 carbon atoms, said aryl substituted by one or two alkyl of 1 to 8 carbon atoms, or phenylalkyl of 7 to 15 carbon atoms, or a group of formula II

where $R_2$, $R_3$, $R_4$ and $R_5$ are as defined above.

8. A compound according to claim 7 wherein R, R' and R" are independently alkyl of 1 to 4 carbon atoms or phenyl, $R_2$ and $R_3$ are independently hydrogen, alkyl of 1 to 17 carbon atoms or phenyl, $R_4$ and $R_5$ are independently hydrogen, alkyl of 1 to 18 carbon atoms, cycloalkyl of 5 to 7 carbon atoms, phenyl, phenyl substituted by alkyl of 1 to 4 carbon atoms, or benzyl, and $R_6$ is alkyl of 4 to 18 carbon atoms, benzyl or a group of formula II where $R_2$, $R_3$, $R_4$ and $R_5$ are as defined above.

9. A compound according to claim 8 wherein R, R' and R" are independently methyl, tert-butyl or phenyl, $R_2$ is hydrogen or methyl, $R_3$ is hydrogen, alkyl of 1 to 17 carbon atoms or phenyl, $R_4$ and $R_5$ are independently hydrogen, alkyl of 1 to 18 carbon atoms, phenyl or benzyl, and $R_6$ is alkyl of 4 to 18 carbon atoms, benzyl or a group of formula II where $R_2$, $R_3$, $R_4$ and $R_5$ are as defined above.

10. The compound according to claim 7 which is dibenzyl P-(N-benzyl-N-tert-butyldimethylsilyloxyaminomethyl)phosphonate.

11. The compound according to claim 7 which is dibenzyl P-(N-benzyl-N-tert-butyl-dimethylsilyloxymethoxyaminomethyl)phosphonate.

* * * * *